United States Patent [19]

Kuo et al.

[11] 4,190,708
[45] Feb. 26, 1980

[54] PRODUCTION OF UROKINASE

[75] Inventors: Mau-Jung Kuo, Creve Coeur; Margaret J. Reents, Chesterfield; Joseph Feder, University City, all of Mo.

[73] Assignee: Monsanto Company, St. Louis, Mo.

[21] Appl. No.: 909,137

[22] Filed: May 24, 1978

[51] Int. Cl.² ............................................. C07G 7/026
[52] U.S. Cl. ..................................................... 435/215
[58] Field of Search ....................... 195/66 B, 1.7, 1.8

[56] References Cited

U.S. PATENT DOCUMENTS

| | | | |
|---|---|---|---|
| 3,904,480 | 9/1975 | Hull et al. | 195/66 B |
| 3,930,944 | 1/1976 | Nicol | 195/1.7 |
| 3,930,945 | 1/1976 | Lewis | 195/1.7 |

OTHER PUBLICATIONS

Barlow et al. article in Coldspring Harbor Conference on Cell Proliferation, vol. 2, 1975, pp. 325–331.

*Primary Examiner*—Lionel M. Shapiro
*Attorney, Agent, or Firm*—Scott J. Meyer; James W. Williams, Jr.

[57] ABSTRACT

The yield of urokinase produced by cell culture of kidney cells is improved by incorporating in the cell culture medium an elevated level of phenylalanine.

4 Claims, No Drawings

PRODUCTION OF UROKINASE

BACKGROUND OF THE INVENTION

This invention relates to a method for the production of urokinase.

Urokinase is an enzyme capable of converting plasminogen into plasmin. As such, it has been found useful as an activator for promoting the lysis of blood clots.

Urokinase occurs in small amounts in human urine, but it has been calculated that isolation of the enzyme from that source requires at least 1500 liters of urine per clinical dose of the enzyme.

More recently, urokinase has been obtained from cultures of kidney cells from various animals such as, e.g. mouse kidney, baby hamster kidney and, in particular, human embryonic kidney (HEK) cells. It has been shown that urokinase isolated from HEK cells grown in tissue culture is identical to urokinase from urine. Barlow and Lazer, *Thromb. Res.* 1 (3), 201–7 (1972).

Various methods have been suggested heretofore to improve the production of urokinase by cell culture techniques. According to one such method described in U.S. Pat. No. 3,904,480, various antimitotic agents are employed in the cell culture medium to increase the yield of plasminogen activator (urokinase). In another approach to the problem, the kidney cell culture is overlayed with fibrin to increase the urokinase yield. Bernik and Kwaan, *J. Lab. Clin. Med.* 70, 650 (1967); *J. Clin. Invest.* 48, 1740 (1969); *J. Clin. Invest.* 52, 823 (1973). Other materials heretofore suggested for addition to the cell culture medium in specified amounts for increasing the yield of urokinase are pronase, as described in U.S. Pat. No. 3,930,944, and glycine, as taught in U.S. Pat. No. 3,930,945.

Still another method for improving the production of urokinase involves selection of cells that produce the enzyme and elimination of non-producers, as described by Barlow et al., "Production of Plasminogen Activator by Tissue Culture Techniques", in "Proteases and Biological Control", Cold Spring Harbor Conference on Cell Proliferation, Vol. 2, 1975, Cold Spring Harbor Lab. (eds. Reich, Rifkin and Shaw), at pages 325–31. The latter publication also indicates that the addition of extra amounts of amino acids such as aspartic acid and glutamic acid do not increase the production of plasminogen activator but that addition of plasminogen and other proteases did increase the yield. U.S. Pat. No. 3,930,940 similarly teaches that amino acids other than glycine (none specified) have no or sometimes opposite effects on urokinase production.

BRIEF DESCRIPTION OF THE INVENTION

In accordance with the present invention, it has been found unexpectedly that by the use of specified additional amounts of the aromatic amino acid phenylalanine in the kidney cell culture medium, the yield of urokinase can be increased to levels substantially greater than obtained with equivalent amounts of glycine. This discovery is all the more surprising because use of additional amounts of certain other amino acids such as aspartic acid, glutamic acid, methionine and histidine provide little or no increase in the yield of urokinase over that obtained without the use of any supplemental amounts of these amino acids. The improved yield with phenylalanine is obtained notwithstanding the fact that the number of cells in the culture (cell density) decreases over time.

DETAILED DESCRIPTION OF THE INVENTION

In a general embodiment of the invention, live kidney cells known to produce urokinase are incubated in a suitable growth medium at about 35°–37° C. in tissue culture flasks until the cells reach confluency. Medium 199 prepared according to the method of Morgan, Morton and Parker, *Proc. Soc. Exptl. Biol. Med.* 73, 1 (1950) is a typically suitable growth medium. Dulbecco's Modified Eagle Medium, McCoy's Medium 5A, Waymouth's MB752/1 Medium, and similar such conventional tissue culture media as described, for example, by Morton, *In Vitro* 6 (2) 89–108 (1970), also can be used. During the growth period, the culture medium advantageously is fortified with mammalian serum, for example, fetal bovine serum generally in an amount of about 5%–15% by volume of the medium.

After the cells have reached confluency, they are washed with a physiologically acceptable wash solution, for example, buffered saline, and the wash liquor is then replaced with a maintenance medium.

Any aqueous nutrient medium known to be useful for maintaining the kidney cells and their production of urokinase can be employed. Preferably, this medium comprises lactalbumin hydrolysate, human serum albumin, glucose, and sodium bicarbonate. Protein hydrolysates other than lactalbumin hydrolysate also can be used such as, for example, tryptone, tryptose, peptone and the like materials.

In accordance with the invention, the maintenance medium is supplemented with an elevated amount, preferably from about 0.3% to 0.7% by weight, of phenylalanine to obtain the desired improved yield of urokinase described above. This is equivalent to about 60–140 times the amount of phenylalanine in Medium 199. Most preferably, about 0.5% phenylalanine is employed in the maintenance medium. Levels substantially in excess of these amounts are believed to be toxic to the cells.

The following examples will further illustrate the invention although it will be understood that the invention is not limited to the specific details of these examples.

EXAMPLE 1

Normal primary human embryonic kidney (HEK) cells, supplied by Grand Island Biological Co. (GIBCO) in suspension, were centrifuged and resuspended in Medium 199 containing 10% by volume of fetal bovine serum. The serum was supplied by KC Biologicals, Inc., Lenexa, Kansas. The cell suspension was used to inoculate 75 cm² Falcon plastic flasks (T-75 flasks) containing the same medium in amounts such that the final volume of the culture and the cell density fell in the ranges of 15–20 ml. and $1.5-2.0 \times 10^5$ cells per ml, respectively. The flasks were incubated at 37° C. in an incubator with 5% $CO_2$ in air. Medium in the flasks was changed every two to three days until the cultures reached confluency. The cells in each flask were then washed with 25 ml. of sterile physiologically normal saline solution (Fisher Scientific Co., catalog no. SO-S-442).

After removal of the wash solution, 10 ml. of the maintenance medium consisting of 13.65 grams per liter of lactalbumin hydrolysate medium (GIBCO catalog no. M-11), 2.2. grams per liter of NaHCO$_3$, 0.1 weight percent of human serum albumin (HSA) (Sigma Chemical Co., catalog no. A-2386), 0.1 weight percent of D-glucose and 0.5 weight percent of L-amino acid (either phenylalanine, methionine, histidine or glycine as stated below in Table 1). The maintenance medium was sampled for urokinase titers and renewed daily with 10 ml. of the same fresh maintenance medium. At the end of the four day cell culture period, the medium was removed and the cells in each flask were washed with 25 ml of the saline solution several times, and then digested with 1 N NaOH solution. DNA (deoxyribonucleic acid) assays were then made, with the DNA content of HEK cells being taken at the usual standard of: 9 μg (micrograms) DNA = 10$^6$ cells. Urokinase titers in Table 1 were then expressed in ml per day per μg of DNA.

The urokinase assay was made by a 2-step iodinated fibrin plate method. In the first step, urokinase acts on plasminogen to form plasmin. In the second step, the plasmin then hydrolyzes a radioactively tagged clotted fibrinogen (fibrin) to release $^{125}$I fibrinopeptides into solution which are measured in a gamma counter. The urokinase activity is then related proportionally to the radioactivity released into solution. One unit of urokinase activity is defined as that amount of the enzyme which hydrolyzes one microgram of the fibrin per hour. This assay procedure is derived from a general procedure for measuring cell factor activity based on fibrinolysis of an $^{125}$I fibrin plate described by Unkeless et al., *J. Exptl. Med.* 137 (1), 85–111 (1973) and a general procedure for iodinating fibrinogen described by Helmkamp et al, *Cancer Res.* 20, 1495–1500 (1960).

Table 1

| Amino Acid | Urokinase Titers | | | | Total DNA* |
|---|---|---|---|---|---|
| | Day 1 | Day 2 | Day 3 | Day 4 | μg |
| Phenylalanine | 37.85 | 46.8 | 33.55 | 37.2 | 80.95 |
| Methionine | 15.3 | 7.2 | 7.6 | 10.4 | 79.0 |
| Histidine | 11.9 | 12.6 | 13.5 | 8.2 | 71.5 |
| Glycine | 10.7 | 11.4 | 16.4 | 33.3 | 67.8 |

*Final DNA content of the cells in each flask ater 4 days of culture in the maintenance medium.

EXAMPLE 2

Normal primary HEK cells were grown to confluency in the T-75 flasks as described in Example 1, above, and similarly washed in sterile saline solution and removed.

Thirty ml. of maintenance medium was added to each flask. The medium was renewed with fresh medium to the same 30 ml. volume every three days. After nine days of culture in the maintenance medium, the cells were digested for DNA assays and the urokinase titers were determined as in Example 1.

In this example, the maintenance medium consisted of 13.75 grams per liter of lactalbumin hydrolysate medium, 2.2 grams per liter of NaHCO$_3$ and 0.1 weight percent of D-glucose. Amino acid and/or HSA were added to the basal maintenance medium to the desired final concentration (weight percent) as shown in Table 2, below. As in Example 1, the urokinase activities are per ml. per day per μg of DNA.

Table 2

| Additives | Urokinase Titers | | | Total DNA* |
|---|---|---|---|---|
| | Day 3 | Day 6 | Day 9 | μg |
| None | 6.1 | 3.6 | 3.1 | 285.8 |
| 0.1% HSA | 13.5 | 7.4 | 4.8 | 298.5 |
| 0.1% HSA + 0.3% Gly. | 22.4 | 11.9 | 11.7 | 308.3 |
| 0.1% HSA + 0.5% Gly. | 26.3 | 24.8 | 17.0 | 264.0 |
| 0.1% HSA + 0.3% Phe | 22.2 | 25.6 | 16.4 | 223.8 |
| 0.1% HSA + 0.5% Phe | 61.2 | 35.6 | 36.3 | 126.0 |
| 0.3% Gly | 13.1 | 14.0 | 7.4 | 287.0 |
| 0.5% Gly | 27.2 | 10.5 | 9.0 | 296.3 |
| 0.3% Phe | 24.4 | 16.1 | 10.1 | 205.5 |
| 0.5% Phe | 46.7 | 27.0 | 19.9 | 118.8 |

*Final DNA content of the cells in each flask after 9 days of culture in the maintenance medium.
Gly = glycine
Phe = phenylalanine It will be seen from the above examples that the yield of urokinase from the kidney cell culture when using elevated levels of phenylalanine in the maintenance medium is substantially greater than with the other amino acids glycine, methionine and histidine. This improvement is obtained even though the number of cells (shown by DNA content) decreases over time.

Various other examples of the present invention will be apparent to the person skilled in the art after reading the instant disclosure without departing from the spirit and scope of the invention. It is intended that all such further examples be included within the scope of the appended claims.

What is claimed is:

1. In a process for the production of urokinase by the culture of live kidney cells in an aqueous nutrient medium, the improvement which comprises adding phenylalanine in an elevated amount of from about 0.3 to about 0.7 weight percent to the said nutrient medium to thereby increase the yield of urokinase.

2. The method of claim 1 in which the phenylalanine is used in an amount of about 0.5 weight percent.

3. The method of claim 1 in which the cells are normal primary human embryonic kidney cells.

4. The method of claim 3 in which the medium comprises lactalbumin hydrolysate, human serum albumin, glucose and sodium bicarbonate.

* * * * *